United States Patent [19]

Bethke et al.

[11] Patent Number: 5,041,537

[45] Date of Patent: Aug. 20, 1991

[54] METHOD OF PREPARING A HIGH-PURITY, VIRUS SAFE, BIOLOGICALLY ACTIVE TRANSFERRIN PREPARATION

[75] Inventors: Ulf Bethke, Babenhausen; Norbert Kothe, Kronberg; Dieter Rudnick, Rödermark; Wolfgang Möller, Oberursel/Ts.; Michael Kloft, Darmstadt, all of Fed. Rep. of Germany

[73] Assignee: Biotest Pharma GmbH, Dreieich, Fed. Rep. of Germany

[21] Appl. No.: 249,807

[22] Filed: Sep. 27, 1988

[30] Foreign Application Priority Data

Oct. 1, 1987 [DE] Fed. Rep. of Germany ....... 3733181

[51] Int. Cl.$^5$ ................................................. C07K 3/00
[52] U.S. Cl. .................................... 530/394; 530/412; 530/416
[58] Field of Search ......................................... 530/394

[56] References Cited

U.S. PATENT DOCUMENTS 3,959,249  5/1976  Antonini ............................. 530/394
4,540,573  9/1985  Neurath et al. ...................... 530/394
4,841,026  6/1989  Van Beveren et al. ............. 530/394

FOREIGN PATENT DOCUMENTS 0099445  2/1984  European Pat. Off. .
0142059  5/1985  European Pat. Off. .
3033932  3/1982  Fed. Rep. of Germany .

OTHER PUBLICATIONS

Deutsche Medizinische Wochenschrift, 110, (1985), pp. 55-63.
Reviews of Infectious Diseases, 5, (1983), No. 1, pp. 92-107.
The Journal of Biological Chemistry, 242, (1967), No. 10, pp. 2507-2513.
Vox Sanguinis, 6, (1961), pp. 24-52.
Vox Sanguinis, 5, (1960), pp. 403-415.
Journal of Immunological Methods, 65, (1983), pp. 55-63.
Methods in Enzymology, LVIII, (1979), pp. 44-93.

*Primary Examiner*—Sam Rosen
*Attorney, Agent, or Firm*—Sprung Horn Kramer & Woods

[57] ABSTRACT

To provide a simple method of preparing biologically active transferrin that can be employed on an industrial scale and that will result in extremely pure and natural transferrin containing no viruses and appropriate for both in-vitro and in-vivo applications, the γ-globulins are precipitated from the fraction containing the transferrin, the precipitant is removed from the residual liquid by ultrafiltration or gel filtration, the liquid is adjusted to a prescribed ionic concentration and protein concentration and (a) treated with β-propiolactone and the solution is subjected to ultraviolet radiation or (b) treated with specific detergents and subjected to ion-exchange chromatography, and the transferrin is concentrated and filtered sterile.

6 Claims, 3 Drawing Sheets

METHOD OF PREPARING A HIGH-PURITY, VIRUS SAFE, BIOLOGICALLY ACTIVE TRANSFERRIN PREPARATION

The invention relates to a method of preparing a high-purity, virus-safe, biologically active, transferrin preparation from plasma fractions that contain transferrin.

Transferrin is the protein that transports iron in human and animal plasma, in which its concentration is approximately 2.5 g/l. This major function of transferrin derives from its ability to specifically bind trivalent iron. Once iron is resorbed into the small intestine or picked up by the iron-storage protein ferritin, it is transported in the trivalent form to other tissues.

Transferrin also has other functions. It participates in preventing infections, promotes cell growth, and is a potential diagnostic agent (K. Theobold & W. König, DMW 110 [1985], 41, 1581).

This wide spectrum of activity makes it desirable to be able to prepare large amounts of high-purity native transferrin for use in therapy and diagnosis. In attaining this objective it is of essential importance to maintain the delicate biological activity of the transferrin, which is measurable in term's of its iron-binding ability, as completely as possible.

As in the case of any protein fraction obtained from human plasma, there is a risk of transmitting such infections as hepatitis B, hepatitis non-A and non-B, and AIDS, and any method of preparing transferrin must include an extremely effective step involving the separation or inactivation of infectious viruses.

Essentially three methods of sterilizing plasma proteins are now known: heat-inactivation in the wet and dry states, sterilization with detergents, and a combination of treatment with $\beta$-propiolactone and ultraviolet radiation (EPA 0 142 059, EPA 0 099 445, & DE 3 033 932).

Plasma proteins are delicate and can only be heatinactivated in conjunction with stabilizers, which can in certain circumstances actually protect the viruses against inactivation, and this method can accordingly not always be considered reliable.

Treatment with detergents or with $\beta$-propiolactone and ultraviolet radiation on the other hand is possible without stabilizers and has proved to be an effective step for inactivating the viruses (DE 3 033 932 and A.M. Prince et al, Rev. Infect. Dis. 5 [1983], 1, 92).

The literature describes various methods of preparing transferrin with plasma or Cohn's paste IV as the starting material and involving various steps of precipitation and adsorption. W. E. Roop and F. W. Putnam (J. Biol. Chem. 242 [1967], 2507), for example, describe a method that employs human plasma as a starting material and consists of precipitation by means of Rivanol and ammonium sulphate followed by exclusion chromatography and ion-exchange chromatography.

Kistler et al (Vox Sang. 5 [1960], 403) describe a similar method employing precipitation with Rivanol and alcohol. The resulting transferrin fraction is 85% pure, and it is further purified by crystallization.

J. K. Inman et al (Vox Sang. 6 [1961], 34) start with paste IV (Cohn's alcohol precipitation) and purify the transferrin by way of alcohol along with precipitation with calcium hydroxide and zinc acetate, with final purification through batch-by-batch adsorption onto cation and anion exchangers. The product is approximately 93% pure.

Other methods described in the literature are based on combinations of precipitation and adsorption.

All of the known methods have decisive drawbacks. On the one hand, the purity and yield are often unsatisfactory. On the other, the methods are often too expensive to be appropriate for economical industrial-scale preparation.

One serious drawback to all the methods is the absence of virus-inactivating steps, subjecting their therapeutic use to the risk of transmitting infections.

Only Inman et al, supra, describe a heatinactivation step, which is restricted, however, to ironsaturated transferrin. Since iron-free transferrin is also necessary for therapeutic purposes, his method is not generally applicable.

Furthermore, tests indicate (FIG. 1) that heat treatment will create aggregates even in iron-saturated transferrin solutions that can produce incompatibility reactions in intravenous application.

The increased viscosity reported by Inman et al confirms this finding.

The object of the invention is to provide a simple method of preparing biologically active transferrin that can be employed on an industrial scale and that will result in extremely pure and natural transferrin containing no viruses and appropriate for both in-vitro and in-vivo applications.

The transferrin can either contain or not contain iron.

This object is attained in accordance with the invention in a method of the aforesaid type starting with transferrin-containing plasma, comprising a) removing the $\gamma$-globulins from the fraction that contains the transferrin by precipitation, b) removing the precipitant from the residual liquid by ultrafiltration or gel filtration, c) adjusting the liquid to an ionic concentration of 0.005 to 0.5 M and to a protein concentration of 10 to 60 g/l and d) treating the liquid with (i) 0.01 to 0.5% $\beta$-propiolactone at a pH of 6.0 to 9.0, adjusting the protein concentration to 2 to 25 g/l and then subjecting the solution to ultraviolet radiation at 254 nm, or (ii) 0.05 to 5% tri-n-butyl phosphate and 0.03 to 0.4% sodium cholate or 0.1 to 5% e) subjecting the solution to ion-exchange chromatography, with an ionic strength that ensures that all the proteins except the transferrin are adsorbed, and f) concentrating and sterile filtering the transferrin.

Although blood plasma has admittedly been protected against viral contamination with highly satisfactory results as previously described herein by such sterilization procedures as treatment with detergents or $\beta$-propiolactone plus ultraviolet radiation, it has previously been impossible to maintain the very delicate biological activity of the transferrin preparation when sterilizing it. It would, rather, have been expected that the transferrin would be denatured.

To obtain a high-purity transferrin preparation it is extremely necessary to separate the companion proteins. It has been discovered that this can be done with unexpected success by means of ion-exchange chromatography. It has also been discovered that it is important to carry out the ion-exchange purification subsequent to sterilization because any proteins that become denatured or modified during sterilization can be separated at that time.

The starting material is a plasma fraction that contains transferrin and is obtained by precipitation—by alcohol fractionation in accordance with Cohn's method, that is, or by means of ion exchangers for example.

This fraction is freed of immunoglobulins as far as possible by treating it with an immunoglobulin precipitant of the type known from Roop et al or Kistler et al, supra, for example—ammonium sulfate, polyethylene glycol (PEG), or 2-ethoxy-6,9-diaminoacridine DL-lactate (Rivanol) for instance.

Once the precipitate has been separated, the residue is freed of precipitant by gelfiltration or gelfiltration on ultrafiltration membranes, which can be flat or hollow-fiber membranes and adjusted to a low ionic concentration of 0.005–0.5 M/l and to a protein concentration of 10–60 g/l.

This solution is treated at a pH of 6–9 with βpropiolactone at a concentration of 0.01–0.5%.

The solution is diluted to a protein level of 2–25 g/l and irradiated at 254 nm in a continuous-flow ultraviolet-irradiation apparatus.

Instead of being treated with β-propiolactone and ultraviolet radiation, the solution can be sterilized with detergents—tri-n-butyl phosphate (0.05–5%) and sodium cholate (0.03–0.4%) or polyoxyethylenesorbitan-monooleate (Tween 80 ®, 0.1–5%) for example.

The transferrin is then further purified, especially to separate albumin and other companion proteins, by means of ion-exchange chromatography at an ionic strength that ensures that all the proteins except the transferrin are adsorbed. This step can be carried out in a column or batch-by-batch. Appropriate adsorbents are such commercially available anion exchangers with DEAE and QAE or QMA groups as DEAE-Trisacryl-LS ®, QMA-Accell ®, Q-Sepharose ®, DEAESephadex ®, QAE-Eupergit ®, etc.

The diluted transferrin fraction so obtained is diafiltered or gelfiltered to remove buffers against physiologically compatible salt solutions and concentrated by ultrafiltration The iron can optionally be removed during this step by adjusting to a pH of 4.0–7.0, treatment with a complexing agent such as ethylenediaminetetraacetic acid (EDTA) sodium salt, and then diafiltered or gelfiltered.

A transferrin preparation obtained in accordance with the invention is distinguished by the following properties:

TABLE 2

| Protein | 150 g/l |
|---|---|
| Transferrin | 150 g/l |
| IgG | 0.025 g/l |
| IgA | 0 g/l |
| IgM | 0 g/l |
| Albumin | 0 g/l |
| Cellulose acetate film electrophoresis (CAF) | 100% β-globulin |
| Proteolytic activity | 17 U/l |
| Plasmin | negative |
| Plasminogen | negative |
| Thrombin | negative |
| PKA | negative |
| Complement-binding reaction | 2 μl complement/mg protein |
| Iron-binding ability | 80% |

The effectiveness of sterilization with β-propiolactone and ultraviolet irradiation was determined by means of bacteriophages. The decrease was 7.5 $\log_{10}$ for the bacterial viruses Φ-X 174, Φ-e, and K, representing adequate virus elimination for hepatitis B, hepatitis non-A and non-B, and AIDS.

As mentioned hereinabove, it was surprisingly discovered that the method of preparing a high-purity, sterilized, and virus-safe transferrin in accordance with the invention does not affect the biological activity of the protein.

If, for example, a Cohn's paste IV containing transferrin with an activity of approximately 80% is employed as a starting material, the same activity will be observed in the purified transferrin.

TABLE 3

|  | iron-binding ability |
|---|---|
| Initial | 83% |
| After sterilization | 80% |
| Final product | 80% |

A transferrin preparation obtained in accordance with the invention was employed as a growth factor in a culture medium.

Generally, transformed and non-transformed mammalian cells are cultured in a medium containing heterological serum, calf's serum for example. The serum naturally contains the growth factor transferrin. It is, however, often desirable, especially when manufacturing drugs for use in humans, to employ a prescribed growth medium that is free of heterological proteins.

Since the growth factor transferrin is absolutely necessary for the propagation of mammalian cells (R. G. Ham et al, Methods in Enzymology, Vol. LVIII, Academic Press, 1979, 44), transferrin must also be present in serum-free media. A transferrin of human provenance suggests itself for the aforesaid purpose in order to avoid sensitization. A sterilized, human, biologically active transferrin is necessary for this application, especially if the product is to be employed for therapeutic purposes in humans.

A transferrin prepared in accordance with the invention was added to a serum-free medium (DMEF-12) and tested for effectiveness on two hybridoma strains. It was surprisingly discovered that transferrin purified and sterilized in accordance with the invention is also appropriate as a growth factor.

The invention will be further explained with reference to the accompanying drawings, wherein:

FIG. 1 is an HPLC graph of iron-saturated transferrin before and after heat treatment for 10 hours at 60° C.;

FIG. 2 is a chart showing cell growth at different concentrations of transferrin as determined after 27 hours, according to T. Mosmann, J. Immunol. Meth. 65 (1983), 55; and FIG. 3 is a chart showing the kinetics of cell growth in media containing transferrin or serum.

Referring now more particularly to the drawings, FIG. 1 shows the difference in the HPLC diagram of an iron-saturated transferrin before and after heat treatment. In addition the materials have the following differences:

TABLE 1

|  | MW > 80 000 D before heat treatment | MW > 80000 D after heat treatment |
|---|---|---|
| iron-saturated transferrin | 10% | 61% |
| iron-free transferrin | 4% | completely denatured. |

Table 4 sets forth the antibody production of hybridoma cells in various culture media, using transferrin in accordance with the present invention.

TABLE 4

Antibody production of hybridoma cells in culture media with and without serum

| Time d | 10% FCS added | 10 mg/l transferrin added | Nothing added |
|---|---|---|---|
| 1 | 4 µg/ml | 4 µg/ml | 4 µg/ml |
| 2 | 11 µg/ml | 12 µg/ml | 11 µg/ml |
| 3 | 14 µg/ml | 17 µg/ml | cell death |
| 4 | 17 µg/ml | 20 µg/ml | cell death |
| 5 | 21 µg/ml | 27 µg/ml | cell death |

Figure 1:
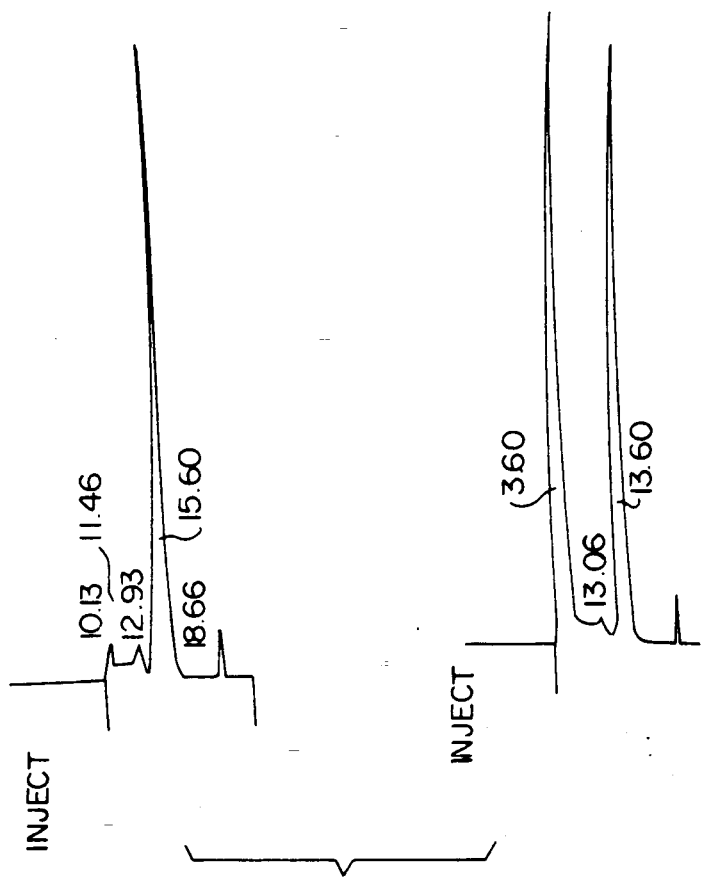
Figure 2:
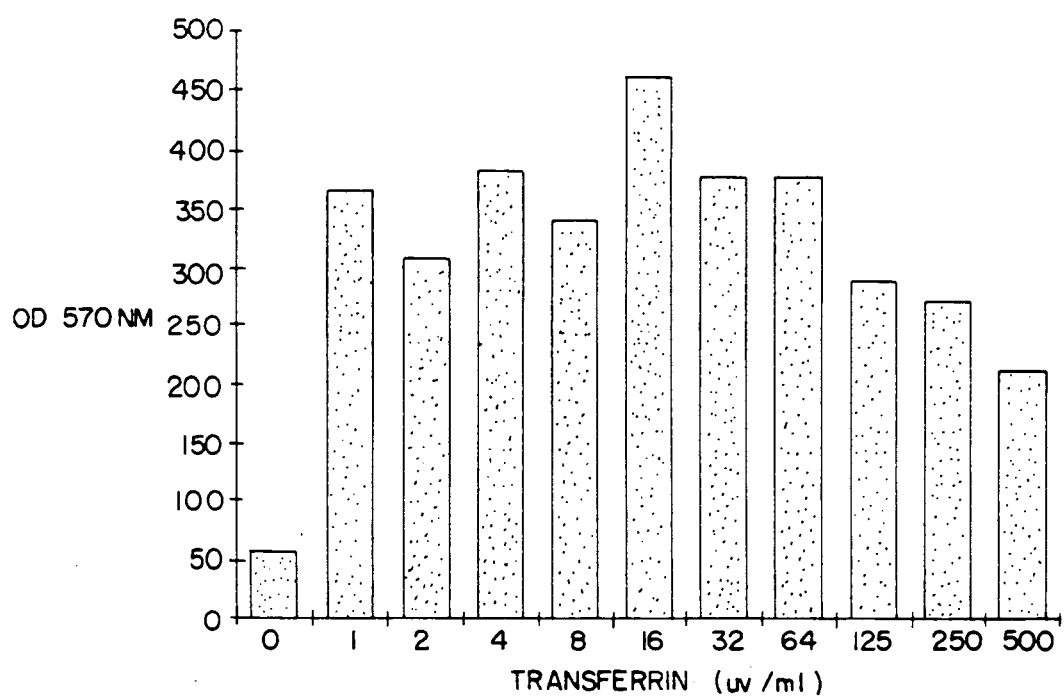
FIG. 2 shows the effectiveness as a cell growth factor of transferrin produced in accordance with the present invention.
Figure 3:
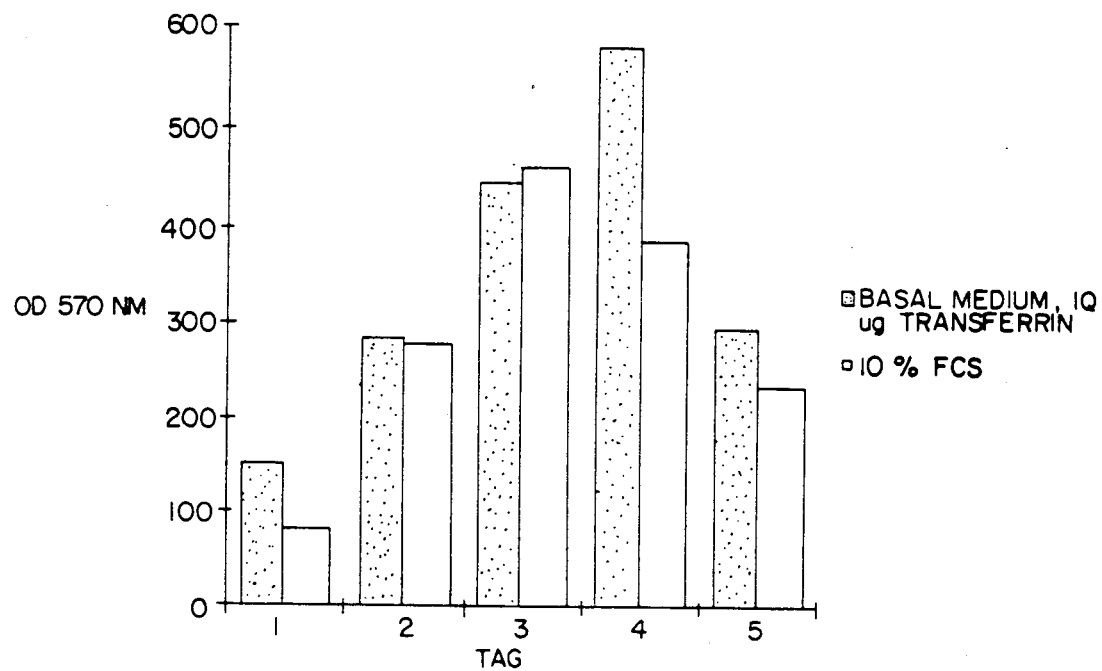
FIG. 3 shows the cell growth kinetics in a medium containing transferrin produced in accordance with the invention and serum.

As will be evident from FIG. 3 and Table 4, not only the growth rates but also the production of monoclonal antibodies are definitely higher than in the medium without transferrin and are also higher than they are in the calf's serum.

Tests in mice and guinea pigs have demonstrated that this high-purity, virus-safe transferrin solution is satisfactorily compatible in intravenous application.

The invention will now be illustrated by the following examples.

Example 1

1 kg of Cohn's paste IV is suspended in 10 times its volume of a buffer (trishydroxyaminomethane, 0.02 M, pH 7.5) and stirred 1 hour. The pH is adjusted to 8.0 with 1 N of sodium-hydroxide solution. Solid ammonium sulfate is added to a concentration of 2.5 M. The batch is stirred 2 hours and allowed to stand overnight at +4° C.

The precipitate is centrifuged out and the residue filtered clear.

The precipitant is removed with an ultrafiltration apparatus (membrane cutoff 10 000 daltons). The batch is adjusted to pH 7.5 with 0.020 M trishydroxyaminomethane and concentrated to a protein content of 40 g/l.

This solution is treated with 1% charcoal filtered clear, adjusted to pH 7.5 with 1 N hydrochloric acid, and treated with 0.05% of β-propiolactone.

The pH is maintained constant for 4 hours and the batch is allowed to stand overnight at +4° C.

The batch is diluted with 0.02 M of TRIS buffer, pH 7.5 to a protein content of 10 g/l and subjected to ultraviolet radiation at 254 nm in a continuous-flow apparatus. The solution is treated with 1.6 g/l of sodium chloride and applied to the anion exchanger DEAE-TrisacrylLS.

The exiting fraction is collected, concentrated to the desired concentration, and filtered sterile.

The bonded iron is removed from this transferrin solution by adjusting the pH to 6.0 and adding an excess of EDTA.

The EDTA and complexed iron is removed in an exclusion-chromatography column packed with Sephadex G-25, and equilibrated with 0.45% sodium chloride.

The protein fraction is collected, concentrated to the desired concentration, and filtered sterile.

| Yield | 75% |
|---|---|
| Cellulose acetate film electrophoresis | 100% β-globulin |
| Protein | 150 g/l |
| Transferrin | 150 g/l |
| Complement-binding reaction | 2 µl compl./mg protein |
| Proteolytic activity | 17 U/l |
| Iron-binding ability | 80% |

Example 2

The procedure is the same as that in Example 1. Subsequent to ultraviolet irradiation of the 1% solution, 2.9 g/l of sodium chloride are added, the pH is adjusted to 6.2, and the batch is treated with 84 ml of DEAE-Sephadex A-50 already equilibrated with 0.05 M of sodium chloride and 0.02 M of TRIS. Subsequent to 2 hours of adsorption, the gel is separated and washed with an equal volume. The filtrates are combined and further processed as described in Example 1.

| Yield | 75% |
|---|---|
| Cellulose acetate film electrophoresis | 100% β-globulin |
| Protein | 150 g/l |
| Transferrin | 150 g/l |
| Complement-binding reaction | 2 µl compl./mg protein |
| Proteolytic activity | 17 U/l |
| Iron-binding ability | 80% |

Example 3

Isolation of the IgG from serum by ion-exchange chromatography results in a fraction rich in β-globulin that can be employed as a starting material for preparing transferrin. This fraction is composed, of 66.1% β-globulin, 6.0% α-globulin, 14.5 γ-globulin, and 13.4% albumin as demonstrated by cellulose acetate film electrophoresis. The transferrin can be isolated from this solution as described in Example 1.

| Yield | 78% |
|---|---|
| Cellulose acetate film electrophoresis | 95.5% β-globulin |
| Protein | 78.3 g/l |
| Transferrin | 75.5 g/l |
| Complement-binding reaction | 5 µl compl./mg protein |
| Proteolytic activity | 10 U/l |
| Iron-binding ability | 72% |

| Yield | 70% |
|---|---|
| Cellulose acetate film electrophoresis | 100% β-globulin |
| Protein | 36.0 g/l |
| Transferrin | 35.2 g/l |
| Complement-binding reaction | 8 µl compl./mg protein |
| Proteolytic activity | 29 U/l |
| Iron-binding ability | 89% |

Example 4

A transferrin can be obtained as described in Example 1 from a mixture of the various starting materials described in Examples 1 and 3.

3.5 l of the β-globulin fraction obtained in Example 3 is added to a suspension of 1 kg of Cohn's paste IV in 10 l of TRIS (0.02 M, pH 7.5). The batch is processed as described in Example 1.

| Yield | app. 75% |
|---|---|

| -continued | |
|---|---|
| Cellulose acetate film electrophoresis | 100% β-globulin |
| Protein | 106 g/l |
| Transferrin | 101 g/l |
| Complement-binding reaction | 8 μl compl./mg protein |
| Proteolytic activity | 25 U/l |
| Iron-binding ability | 85% |

It is understood that the specification and examples are illustrative but not limitative of the present invention and that other embodiments within the spirit and scope of the invention will suggest themselves to those skilled in the art.

We claim:

1. A method of preparing a high-purity, virus-safe biologically active, transferrin preparation from plasma fractions that contain transferrin, comprising
   a) removing the γ-globulins from the fraction that contains the transferrin by precipitation,
   b) removing the precipitant from the residual liquid by ultrafiltration or gel filtration,
   c) adjusting the liquid to an ionic concentration of 0.005 to 0.5 M and to a protein concentration of 10 to 60 g/l and
   d) treating the liquid with (i) 0.01 to 0.5% β-propiolactone at a pH of 6.0 to 9.0, adjusting the protein concentration to 2 to 25 g/l and then subjecting the solution to ultraviolet radiation at 254 nm, or (ii) 0.05 to 5% tri-n-butyl phosphate and 0.03 to 0.4% sodium cholate or 0.1 to 5% polyoxyethylenesorbitanmonooleate,
   e) subjecting the solution to ion-exchange chromatography, with an ionic strength that ensures that all the proteins except the transferrin are adsorbed, and
   f) concentrating and sterile filtering the transferrin.

2. The method according to claim 1, wherein the precipitation is effected with ammonium sulfate or ethanol, thereby to remove the α-globulins.

3. The method according to claim 1, wherein step (e) is anion-exchange chromatography.

4. The method according to claim 1, wherein the chromatography is effected with an ionic concentration of 0.02 to 0.12 M at a pH of 6.0 to 8.0 that ensures that all the proteins except transferrin are adsorbed.

5. The method according to claim 4, wherein the precipitation is effected with ammonium sulfate or ethanol, thereby to remove the α-globulins.

6. The method according to claim 1, wherein between steps e) and f) a complexing agent is added to bind bound iron, followed by ultrafiltration or gel filtration to

* * * * *